(12) United States Patent
Kalathil

(10) Patent No.: US 9,380,969 B2
(45) Date of Patent: *Jul. 5, 2016

(54) SYSTEMS AND METHODS FOR VARYING A SAMPLING RATE OF A SIGNAL

(71) Applicant: Covidien LP, Mansfield, MA (US)

(72) Inventor: Raghunath Mammulli Kalathil, Longmont, CO (US)

(73) Assignee: Covidien LP, Mansfield, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 13/936,887

(22) Filed: Jul. 8, 2013

(65) Prior Publication Data
US 2013/0296668 A1    Nov. 7, 2013

Related U.S. Application Data

(63) Continuation of application No. 12/512,155, filed on Jul. 30, 2009, now Pat. No. 8,494,786.

(51) Int. Cl.
| | | |
|---|---|---|
| *G01N 31/00* | (2006.01) | |
| *G01R 35/00* | (2006.01) | |
| *A61B 5/1455* | (2006.01) | |

(52) U.S. Cl.
CPC ........... *A61B 5/1455* (2013.01); *A61B 5/14551* (2013.01)

(58) Field of Classification Search
CPC .............. G01J 3/28; G01J 3/02; G01N 21/31; G01N 21/359; G01R 35/005; A61B 5/1455
USPC .................................................... 702/28, 106
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |

(Continued)

FOREIGN PATENT DOCUMENTS

| | | |
|---|---|---|
| DE | 19640807 | 9/1997 |
| EP | 0615723 | 9/1994 |

(Continued)

OTHER PUBLICATIONS

Aoyagi, T., et al.; "Analysis of Motion Artifacts in Pulse Oximetry," Japanese Society ME, vol. 42, p. 20 (1993) (Article in Japanese—contains English summary of article).

(Continued)

*Primary Examiner* — Michael Nghiem
(74) *Attorney, Agent, or Firm* — Fletcher Yoder PC

(57) ABSTRACT

Methods and systems are provided that include sampling a light intensity signal at different frequencies based on the waveform of the signal to produce a more accurate digitized signal. The light intensity signal is an analog signal proportional to the intensity of light received at a detector of a pulse oximetry system. In one embodiment, the signal may be sampled exponentially during pulse width periods, such that the end of the pulse width periods where the signal reaches a maximum amplitude may be sampled more frequently. The signal may also be exponentially sampled or oversampled during periods when the signal is expected to near a maximum amplitude. Further, the signal may be sampled less frequently during low amplitude periods of the signal, and during dark periods, such that processing power may be conserved.

6 Claims, 5 Drawing Sheets

(56) References Cited

U.S. PATENT DOCUMENTS

| | | |
|---|---|---|
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| RE33,643 E | 7/1991 | Isaacson et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,348,004 A | 9/1994 | Hollub |
| 5,351,685 A | 10/1994 | Potratz |
| 5,355,880 A | 10/1994 | Thomas et al. |
| 5,365,066 A | 11/1994 | Krueger et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| RE35,122 E | 12/1995 | Corenman et al. |
| 5,482,036 A | 1/1996 | Diab et al. |
| 5,483,646 A | 1/1996 | Uchikoga |
| 5,533,507 A | 7/1996 | Potratz |
| 5,553,614 A | 9/1996 | Chance |
| 5,558,096 A | 9/1996 | Palatnik |
| 5,564,417 A | 10/1996 | Chance |
| 5,575,285 A | 11/1996 | Takanashi et al. |
| 5,577,500 A | 11/1996 | Potratz |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Kuenstner |
| 5,730,124 A | 3/1998 | Yamauchi |
| 5,758,644 A | 6/1998 | Diab et al. |
| 5,766,127 A | 6/1998 | Pologe et al. |
| 5,779,631 A | 7/1998 | Chance |
| 5,782,757 A | 7/1998 | Diab et al. |
| 5,786,592 A | 7/1998 | Hök |
| 5,803,910 A | 9/1998 | Potratz |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,921,921 A | 7/1999 | Potratz et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,229,856 B1 | 5/2001 | Diab et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,476,743 B1 * | 11/2002 | Brown ............... G06K 7/0166 235/449 |
| 6,487,439 B1 | 11/2002 | Skladnev et al. |
| 6,501,974 B2 | 12/2002 | Huiku |
| 6,501,975 B2 | 12/2002 | Diab et al. |
| 6,505,060 B1 | 1/2003 | Norris |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,643,530 B2 | 11/2003 | Diab et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| RE38,492 E | 4/2004 | Diab et al. |
| 6,731,274 B2 | 5/2004 | Powell |
| 6,748,253 B2 | 6/2004 | Norris et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,826,419 B2 | 11/2004 | Diab et al. |
| 6,829,496 B2 | 12/2004 | Nagai et al. |
| 6,839,659 B2 | 1/2005 | Tarassenko et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,003,339 B2 | 2/2006 | Diab et al. |
| 7,024,235 B2 | 4/2006 | Melker et al. |
| 7,027,849 B2 | 4/2006 | Al-Ali |
| 7,027,850 B2 | 4/2006 | Wasserman |
| 7,030,749 B2 | 4/2006 | Al-Ali |
| 7,035,697 B1 | 4/2006 | Brown |
| 7,047,056 B2 | 5/2006 | Hannula et al. |
| 7,060,035 B2 | 6/2006 | Wasserman |

(56) References Cited

U.S. PATENT DOCUMENTS

| | | | |
|---|---|---|---|
| 7,062,307 B2 | 6/2006 | Norris et al. | |
| 7,127,278 B2 | 10/2006 | Melker et al. | |
| 7,142,142 B2 | 11/2006 | Petersen et al. | |
| 7,162,306 B2 | 1/2007 | Caby et al. | |
| 7,209,775 B2 | 4/2007 | Bae et al. | |
| 7,215,985 B2 | 5/2007 | Petersen et al. | |
| 7,221,971 B2 | 5/2007 | Diab et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,295,866 B2 | 11/2007 | Al-Ali | |
| 7,302,284 B2 | 11/2007 | Baker, Jr. et al. | |
| 7,315,753 B2 | 1/2008 | Baker, Jr. et al. | |
| 7,336,982 B2 | 2/2008 | Yoo et al. | |
| 7,373,193 B2 | 5/2008 | Al-Ali et al. | |
| 7,400,919 B2 | 7/2008 | Petersen et al. | |
| 7,800,525 B2 | 9/2010 | Beseke et al. | |
| 8,059,349 B2 | 11/2011 | Annampedu et al. | |
| 8,494,786 B2* | 7/2013 | Kalathil | 702/28 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2005/0004479 A1 | 1/2005 | Townsend et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0143634 A1 | 6/2005 | Baker et al. | |
| 2005/0168722 A1 | 8/2005 | Forstner et al. | |
| 2005/0177034 A1 | 8/2005 | Beaumont | |
| 2005/0187448 A1* | 8/2005 | Petersen et al. | 600/323 |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0195028 A1 | 8/2006 | Hannula et al. | |
| 2006/0211930 A1 | 9/2006 | Scharf et al. | |
| 2006/0217603 A1 | 9/2006 | Nagai et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2006/0287589 A1 | 12/2006 | Wobermin et al. | |
| 2007/0118028 A1 | 5/2007 | Kitajima et al. | |
| 2007/0149872 A1 | 6/2007 | Zhang et al. | |
| 2007/0203417 A1 | 8/2007 | Wasserman et al. | |
| 2007/0225582 A1 | 9/2007 | Diab et al. | |
| 2008/0027502 A1 | 1/2008 | Ransom | |
| 2008/0033265 A1 | 2/2008 | Diab et al. | |
| 2008/0064936 A1 | 3/2008 | Al-Ali | |
| 2008/0081974 A1 | 4/2008 | Pav | |
| 2008/0161663 A1 | 7/2008 | Lee et al. | |
| 2009/0118597 A1 | 5/2009 | Mills et al. | |
| 2011/0123192 A1 | 5/2011 | Rosenthal et al. | |

FOREIGN PATENT DOCUMENTS

| | | |
|---|---|---|
| EP | 0702931 | 3/1996 |
| EP | 1491135 | 12/2004 |
| JP | 2237544 | 9/1990 |
| JP | 3170866 | 7/1991 |
| JP | 3238813 | 10/1991 |
| JP | 4332536 | 11/1992 |
| JP | 6098881 | 4/1994 |
| JP | 7124138 | 5/1995 |
| JP | 7136150 | 5/1995 |
| JP | 2003173536 | 6/2003 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| JP | 2008188216 | 8/2008 |
| WO | WO9309711 | 5/1993 |
| WO | WO9843071 | 10/1998 |
| WO | WO9932030 | 7/1999 |
| WO | WO0021438 | 4/2000 |
| WO | WO2005009221 | 2/2005 |
| WO | WO2005065540 | 7/2005 |
| WO | WO2008137077 | 11/2008 |
| WO | WO2009101678 | 8/2009 |

OTHER PUBLICATIONS

Vincente, L.M., et al.; "Adaptive Pre-Processing of Photoplethysmographic Blood Volume Pulse Measurements," pp. 114-117 (1996).

Barreto, Armando B., et al.; "Adaptive LMS Delay Measurement in dual Blood Volume Pulse Signals for Non-Invasive Monitoring," *IEEE*, pp. 117-120 (1997).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Lutter, N., et al.; "Comparison of Different Evaluation Methods for a Multi-wavelength Pulse Oximeter," Biomedizinische Technik, vol. 43, (1998).

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Todd, Bryan, et al.; "The Identification of Peaks in Physiological Signals," *Computers and Biomedical Research*, vol. 32, pp. 322-335 (1999).

(56) References Cited

OTHER PUBLICATIONS

Goldman, Julian M.; "Masimo Signal Extraction Pulse Oximetry," *Journal of Clinical Monitoring and Computing*, vol. 16, pp. 475-483 (2000).

Belal, Suliman Yousef, et al.; "A fuzzy system for detecting distorted plethysmogram pulses in neonates and paediatric patients," Physiol. Meas., vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

A. Johansson; "Neural network for photoplethysmographic respiratory rate monitoring," Medical & Biological Engineering & Computing, vol. 41, pp. 242-248 (2003).

Hamilton, Patrick S., et al.; "Effect of Adaptive Motion-Artifact Reduction on QRS Detection," Biomedical Instrumentation & Technology, pp. 197-202 (2000).

J. Huang, et al.; "Low Power Motion Tolerant Pulse Oximetry," Abstracts, A7, p. S103. (2002).

Odagiri, Y.; "Pulse Wave Measuring Device," Micromechatronics, vol. 42, No. 3, pp. 6-11 (1998) (Article in Japanese—contains English summary of article).

P. Lang, et al.; "Signal Identification and Quality Indicator™ for Motion Resistant Pulse Oximetry," Anaesthesia and Analgesia, vol. 94, Abstracts, A10, p. S105. (2002).

* cited by examiner

SYSTEMS AND METHODS FOR VARYING A SAMPLING RATE OF A SIGNAL

CROSS-REFERENCE TO RELATED APPLICATIONS

This application is a continuation application of U.S. patent application Ser. No. 12/512,155, entitled "Exponential Sampling of Red and Infrared Signals," filed Jul. 30, 2009, which subsequently issued as U.S. Pat. No. 8,494,786, the disclosure of which is hereby incorporated by reference in its entirety for all purposes.

BACKGROUND

The present disclosure relates generally medical devices and, more particularly, to methods of processing sensed physiological signals.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The intensity of the detected absorbed and/or scattered light may result in an analog signal proportional to the intensity of the detected light, which may be sampled to produce a digitized signal. The digitized signal may be further processed and used to determine the physiological characteristics. Typically, the analog signal may be sampled periodically, such that the sampling density is evenly distributed along the signal. However, the analog signal increases in amplitude during a pulse of emitted light, and generally does not reach the maximum amplitude until the end of a pulse. Thus, the sampling frequency may not sufficiently sample a light intensity signal where the pulse amplitude is the highest.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
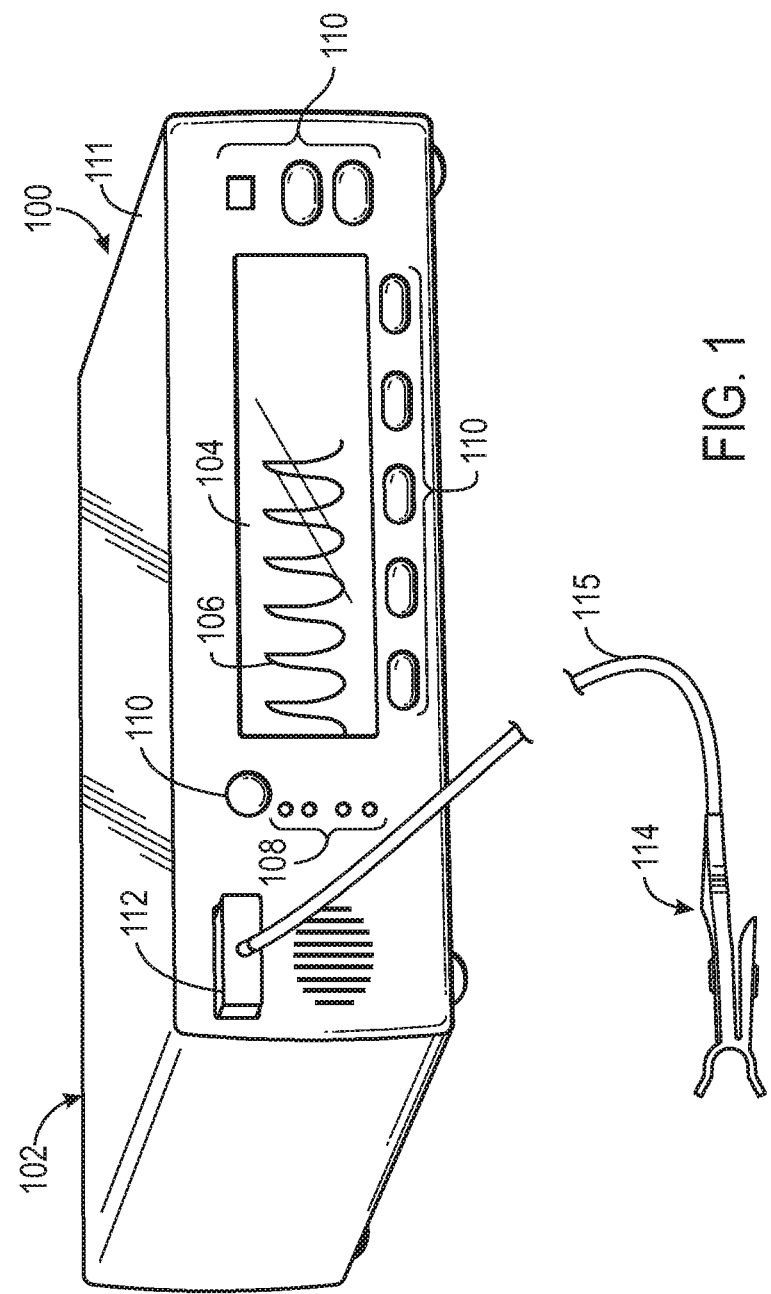
FIG. 1 illustrates a perspective view of a pulse oximeter in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A pulse oximeter emitter may emit one or more lights containing red and infrared (IR) wavelengths into a tissue, and the light that is transmitted and/or scattered by the tissue may be received at a detector. As red and IR light have different wavelengths, and as oxygenated and deoxygenated hemoglobin in the blood absorb different wavelengths of light, certain physiological characteristics such as blood-oxygen saturation and pulse rate may be determined based on the red and IR light received from the tissue. Typically, the detector (e.g., a photodiode) in the pulse oximeter may produce a current proportional to the intensities of the red and IR light received by the detector. The produced current may be the analog signal (also referred to as the "light intensity signal") that is sampled to produce the digitized signal used in further processing and/or calculations to determine the physiological characteristics. For example, the ratio of red and IR light transmitted through the tissue may be computed to determine blood-oxygen saturation in accordance with known techniques.

A pulse oximeter may typically emit red and IR light alternately (i.e., pulses), and a detector may detect the red and IR light that has been transmitted and/or scattered by the tissue. With each pulse of red and IR light emitted by the emitter, the intensity of the red and IR light received at the detector may vary through the pulse width period. Due to certain factors such as opacity of the tissue (optical density of the tissue between the emitter and the detector), and the distance between the emitter and the detector, the amount of emitted light that is transmitted through the tissue may not be fully detected until near the end of the pulse width period. Thus, the light intensity signal, proportional to the intensities of the received red and IR light, may not reach a maximum amplitude until the near the end of the pulse width period. The maximum amplitude of the light intensity signal may include the most significant information in producing an accurate digitized signal. While light intensity signals are typically sampled periodically, periodic sampling may not have a high sampling density during the most significant time of the pulse width period (i.e., when the signal is at or near the maximum amplitude). Further, the sampling density at less relevant times, including the dark portions, may be higher than necessary.

The present techniques relate to systems and methods for sampling a light intensity signal based on the waveform of the signal. In one or more embodiments, the sampling frequency may be higher when the signal is at or approaching a maximum pulse amplitude and lower during less relevant times. For example, the pulse period of light intensity signal may be sampled exponentially, rather than periodically, such that the end of the pulse width period where the signal approaches and reaches the maximum amplitude may be sampled more frequently. In some embodiments, the sampling frequency may be based on the shape of the light intensity signal. For example, at a certain time during a pulse width period, a pulse oximeter may begin exponential sampling, oversampling, or sampling at the Nyquist rate of the signal until the end of the pulse width period. Furthermore, sampling frequency may be lower during portions of the pulse width period when the signal amplitude is lower, and during detection periods outside of the pulse width periods (i.e., dark periods), thus saving on processing power. For example, a pulse oximeter may sample a signal substantially in proportion to an amplitude of the signal during the red pulse width period and the infrared pulse width period and may sample the signal at a substantially constant rate during the dark periods.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
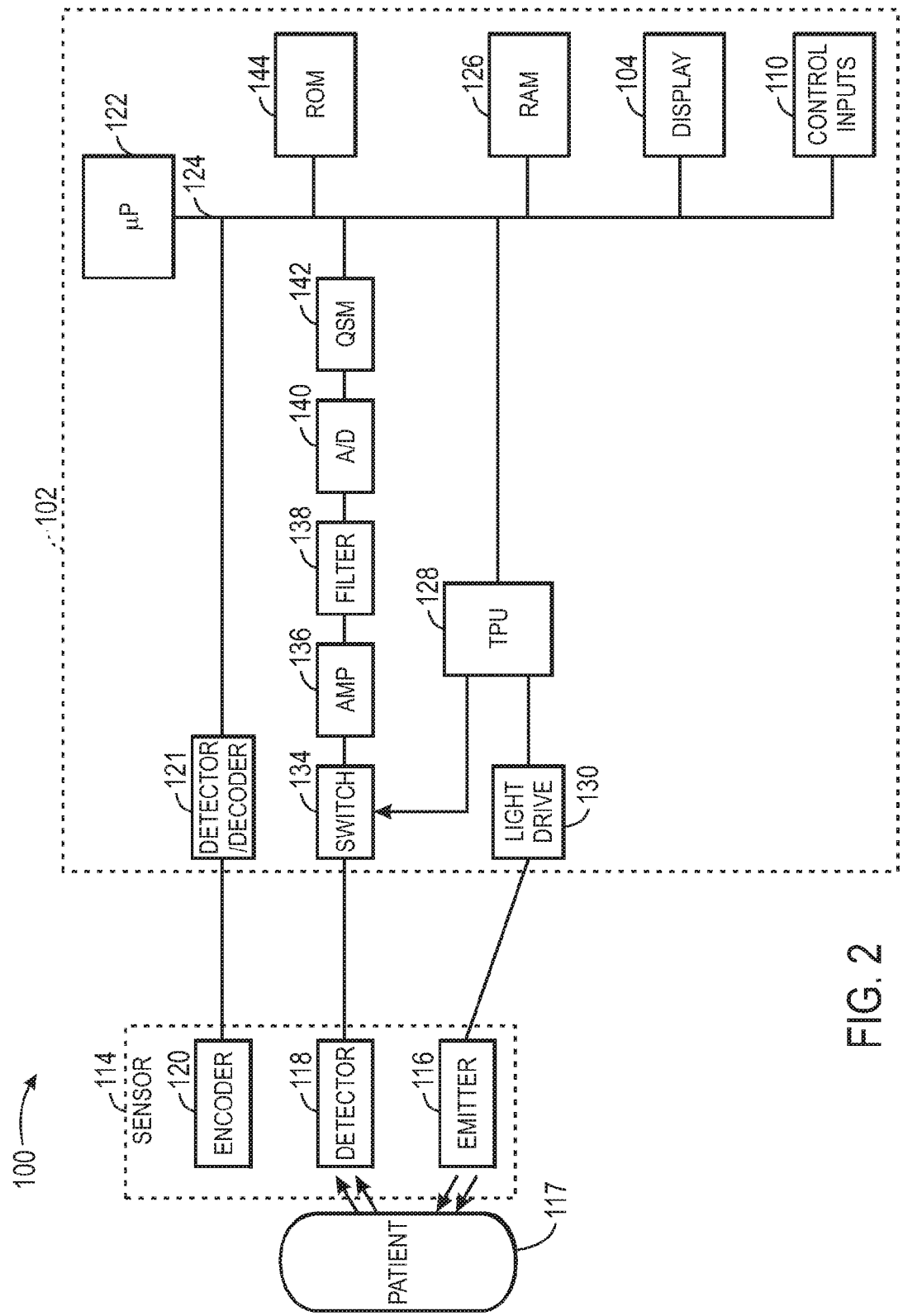
FIG. 2 illustrates a simplified block diagram of a pulse oximeter in FIG. 1, according to an embodiment.

Turning to FIG. 2, a simplified block diagram of a pulse oximeter 100 is illustrated in accordance with an embodiment. Specifically, certain components of the sensor 114 and the monitor 102 are illustrated in FIG. 2. The sensor 114 may include an emitter 116, a detector 118, and an encoder 120. It should be noted that the emitter 116 may be capable of emitting at least two wavelengths of light, e.g., RED and infrared (IR) light, into the tissue of a patient 117, where the RED wavelength may be between about 600 nanometers (nm) and about 700 nm, and the IR wavelength may be between about 800 nm and about 1000 nm. The emitter 116 may include a single emitting device, for example, with two light emitting diodes (LEDs) or the emitter 116 may include a plurality of emitting devices with, for example, multiple LED's at various locations. Regardless of the number of emitting devices, the emitter 116 may be used to measure, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 118 may be an array of detector elements that may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. For example, the detector 118 may comprise one or more photodiodes, or any other element capable of converting light into either a current or voltage. After converting the received light to an electrical signal, the detector 118 may send the signal to the monitor 102, where physiological characteristics may be calculated based at least in part on the absorption of light in the tissue of the patient 117.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. The encoder 120 may, for instance, be a memory on which one or more of the following information may be stored for communication to the monitor 102: the type of the sensor 114; the wavelengths of light emitted by the emitter 116; and the proper calibration coefficients and/or algorithms to be used for calculating the patient's 117 physiological characteristics. In one embodiment, the data or signal from the encoder 120 may be decoded by a detector/decoder 121 in the monitor 102.

Signals from the detector 118 and the encoder 120 may be transmitted to the monitor 102. The monitor 102 may include one or more processors 122 coupled to an internal bus 124. Also connected to the bus may be a RAM memory 126 and a display 104. A time processing unit (TPU) 128 may provide timing control signals to light drive circuitry 130, which controls when the emitter 116 is activated, and if multiple light sources are used, the multiplexed timing for the different light sources. TPU 128 may also control the gating-in of signals from detector 118 through a switching circuit 134. These signals are sampled at the proper time, depending at least in part upon which of multiple light sources is activated, if multiple light sources are used. The received signal from the detector 118 may be passed through an amplifier 136, a low pass filter 138, and an analog-to-digital converter 140 for amplifying, filtering, and digitizing the electrical signals the from the sensor 114. The digital data may then be stored in a queued serial module (QSM) 142, for later downloading to RAM 126 as QSM 142 fills up. In an embodiment, there may be multiple parallel paths for separate amplifiers, filters, and A/D converters for multiple light wavelengths or spectra received.

In an embodiment, based at least in part upon the received signals corresponding to the light received by detector 118, processor 122 may calculate the oxygen saturation using various algorithms. These algorithms may require coefficients, which may be empirically determined For example, algorithms relating to the distance between an emitter 116 and various detector elements in a detector 118 may be stored in a ROM 144 and accessed and operated according to processor 122 instructions.

Figure 3:
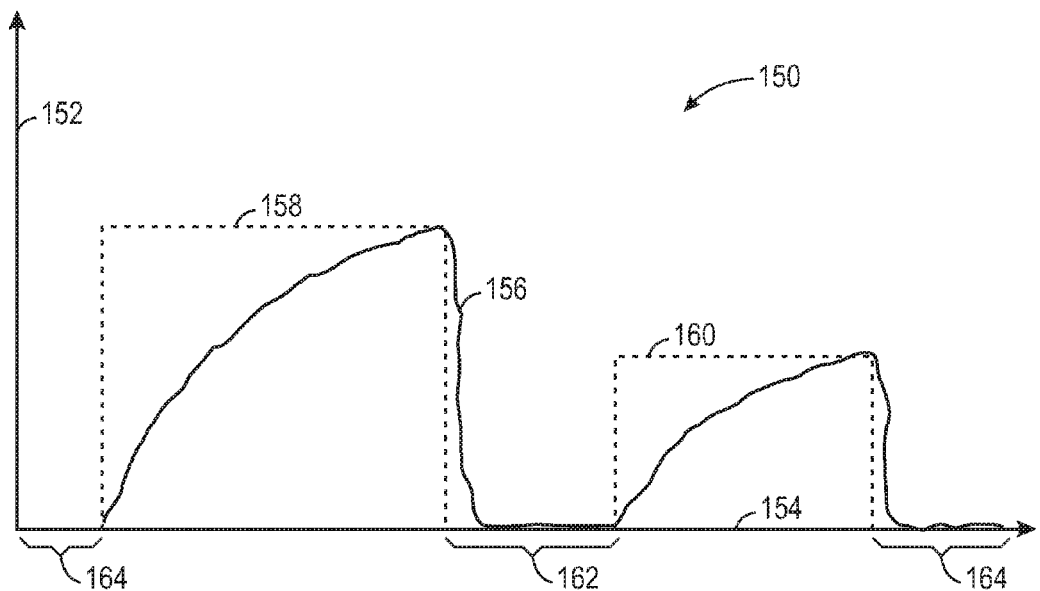
FIG. 3 is a graph depicting the waveform of a light intensity signal received at a pulse oximeter in FIG. 1, according to an embodiment.

In one embodiment, a signal 156 proportional to the intensity of light received by the detector 118 is illustrated in the graph 150 of FIG. 3. As discussed, the detector 118 may be capable of sensing the intensity of light that is emitted by the emitter 116 and transmitted through the tissue of the patient 117. The detector 118 may produce a current, or any other analog signal, that is proportional to the intensity of the received light. This analog signal 156, also referred to as a light intensity signal, may be sampled to produce a digitized signal, which may be suitable for further processing and/or calculations. For example, the processor 122 may apply algorithms to the digitized signal to determine various physiological characteristics.

The light intensity signal 156 may have varying amplitude 152 resulting from the one or more lights (e.g., red and IR light) emitted by the emitter 116 throughout the detection time 154 (x-axis of the graph 150). The amplitude 152 (the y-axis of the graph 150) may be proportional to a current output by the detector 118 in response to the intensity of light received. As discussed, red light and IR light may be used because they have different wavelengths which are absorbed differently by oxygenated and deoxygenated blood. Such absorption characteristics may be useful in determining physiological parameters such as oxygen saturation in the blood. However, some detectors 118 may not differentiate between red light and IR light if both are received simultaneously. To differentiate between the absorption and/or transmission of different lights, the pulse oximeter 100 may alternately turn a red light and an IR light on and off (i.e., pulses), such that when the red light is on, the light received at the detector 118 may be processed as red light (i.e., during the red pulse width period 158), and when the IR light is on, the light received at the detector 118 may be processed as IR light (i.e., during the IR pulse width period 160). Thus, the pulse oximeter 100 may sample during the red pulse width period 158 and the IR pulse width period 160 to produce a digitized signal which contains information of light intensity during each pulse width period 158 or 160. Further, the pulse oximeter 100 may also sample during the dark periods 162 and 164 between the pulse width period periods 158 and 160 to filter out DC content such as ambient light.

The amplitude 152 of the signal 156 may also vary during the red pulse width period 158 and the IR pulse width period 160. The signal 156, corresponding to the intensity of transmitted light received at the detector 118, may not reach a maximum amplitude until near the end of the pulse width periods 158 and 160. Variations of the signal 156 during a pulse width periods 158 and 160 may be based on factors such as the opacity of the tissue (optical density of the tissue between the emitter 116 and the detector 118), the distance between the emitter 116 and the detector 118, etc. Because of these and other factors, the amount of emitted light that is transmitted through the tissue may not be fully detected until near the end of the pulse width periods 158 and 160. Thus, the end portions of the pulse width periods 158 and 160 where the signal 156 approaches a maximum amplitude may contain the most relevant information in accurately determining physiological characteristics.

Figure 4:
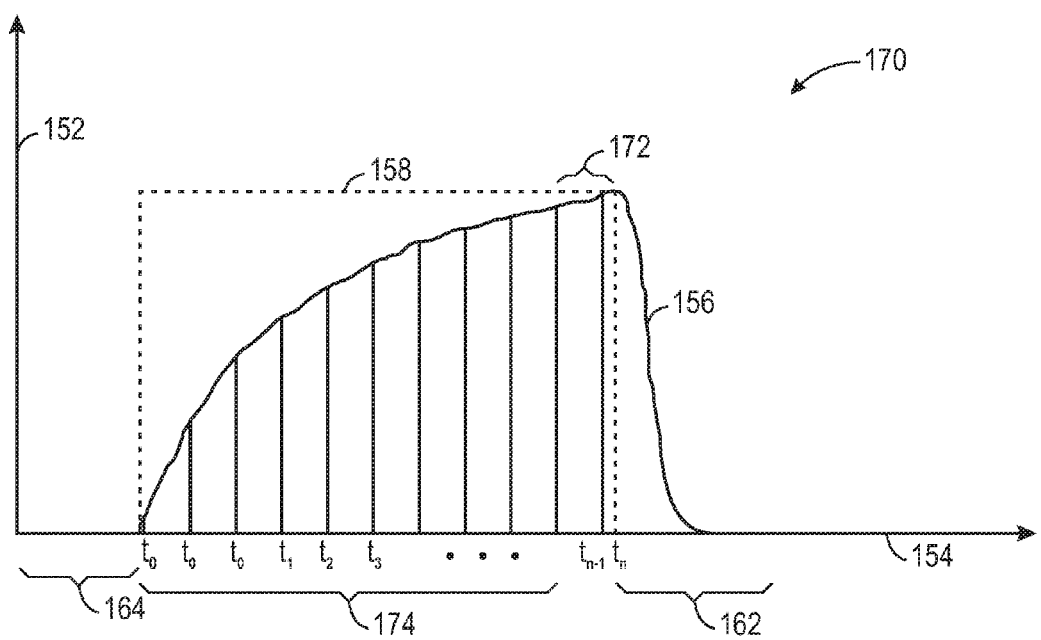
FIG. 4 is a graph depicting periodic sampling of a light intensity signal.

Typically, a pulse oximeter 100 may sample a signal 156 periodically, as depicted in the graph 170 of FIG. 4, which illustrates the sampling of a signal 156 during a red pulse width period 158. However, as discussed, the most relevant portion 172 of the signal 156 may be the portions of the signal 156 approaching or at a maximum amplitude. Thus, a periodic sampling method may result in the even sampling of the signal 156 during the most relevant portions 172 and the comparatively less relevant portions 174 of the signal 156. Such a sampling method may result in a less accurate digital signal if, for example, the periodic sampling method fails to sample a signal 156 during the maximum amplitude of a pulse width period 158. A situation where the maximum amplitude of the signal 156 during the pulse width period 158 is not sampled may have a higher probability of occurring when the sampling density (i.e., the number of samples in a period of time) is lower.

In one or more embodiments of the present techniques, a signal 156 may be sampled based on the waveform of the signal 156, such that the signal 156 may be sampled more frequently at relevant portions 172 (i.e., the portion where the signal 156 approaches or is at a maximum amplitude), and less frequently at less relevant portions 174 (i.e., other portions of the signal 156 in the pulse width period 158 before the signal 156 nears a maximum amplitude). For example, as illustrated in the graph 180 of FIG. 5, the signal 156 may be exponentially sampled during a pulse width period 158, such that the relevant portion 172 of the signal 156 has a higher sampling density than other portions 174 of the signal 156 due to the exponentially increasing sampling frequency within the pulse width period 158. One example of an algorithm used in exponential sampling may be explained in the equation below:

$$f(x, \lambda) = \begin{cases} 1 - e^{-\lambda x} & \text{for } x \geq 0 \\ 0 & \text{for } x < 0 \end{cases} \quad \text{eq. 1}$$

In eq. 1 above, x may represent the number of samples to be performed during a pulse width period 158, and λ may be the rate parameter. In some embodiments, adjusting the rate parameter λ may vary the number of samples taken during the pulse width period 158, and may increase the sampling density during the relevant portion 172 of the signal 156. For example, λ may have values between 1.0 or 1.5, or may be greater for a greater sampling density during the relevant portion 172 of the signal 156 in the pulse width period 158.

In one or more embodiments, the signal 156 may also be sampled with a linearly increasing sampling frequency within the pulse width period 158, or sampled with a sampling frequency that is increased substantially in proportion to an expected increase of the signal 156 during the red pulse width period 158 and the infrared pulse width period 160. For example, the increase in sampling frequency may be based on known characteristics of the waveform of the signal 156, such as the rate the signal 156 increases during a pulse width period 158.

Furthermore, in some embodiments, the sampling frequency in the other portions 174 of the signal 156 may have a sampling frequency that is less than the periodic sampling frequency used in typical pulse oximeters and/or less than the Nyquist sampling frequency. For example, a typical pulse oximeter may sample a signal output from a detector at about 1211 Hz periodically throughout a detection time. Such a sampling frequency may produce an 8 bit digital signal from the sampled analog signal 156. In the present techniques, a pulse oximeter 100 may sample a signal 156 at a higher sampling frequency than 1211 Hz, such as at 4844 Hz (i.e., four times the standard 1211 Hz), when the signal 156 is at the relevant portion 172. The digitized signal may have greater resolution and/or increased accuracy, and may be greater than an 8 bit signal (e.g., 16 bit or 24 bit). The pulse oximeter 100 may also sample the signal 156 at a lower sampling frequency than 4844 Hz (e.g., less than 1211 Hz or not at all), during a less relevant portion 174 of the signal 156 to save on processing power. More efficient sampling may also help in limiting the size of a digitized signal, such that a smaller digitized signal may still contain more samples of relevant portions of the analog signal.

Figure 5:
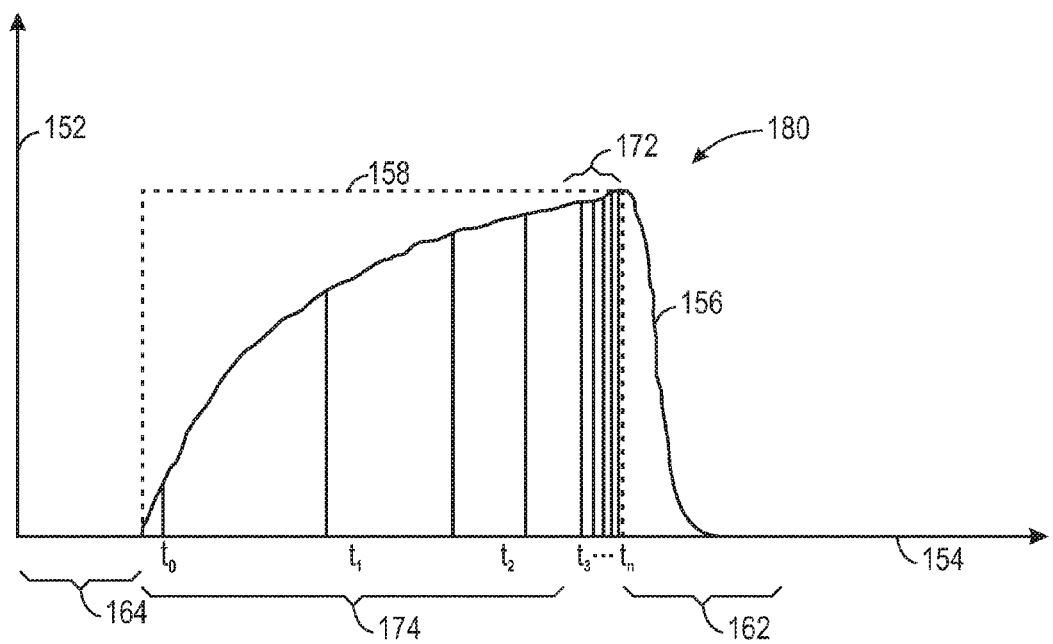
FIG. 5 is a graph depicting exponential sampling of a light intensity signal, according to an embodiment.

A red pulse width period 158 is used in FIG. 5, as well as in FIGS. 6 and 7 below as an example. The present sampling techniques may apply to various portions of a light intensity signal, including an IR pulse width period 160 (as in FIG. 3), or a pulse width period corresponding to any other emitted and/or detected light. Further, the sampling method used in portions of the signal 156 outside of the pulse width period 158, such as dark periods 162 and 164 (FIG. 3) may be periodic (not shown). For example, the signal 156 may be sampled at a substantially constant rate during the dark periods 162. The sampling density may also be lower than the sampling density used during the relevant portion 172 of the signal, as a high sampling density during dark periods 162 and 164 may not be as useful a high sampling density during the relevant portion 172 for producing an accurate digitized sample. The dark periods 162 and 164 may still be sampled so that the DC content, such as any noise or interferences resulting from ambient light, may be removed before computing physiological data from the digitized signal.

Figure 6:
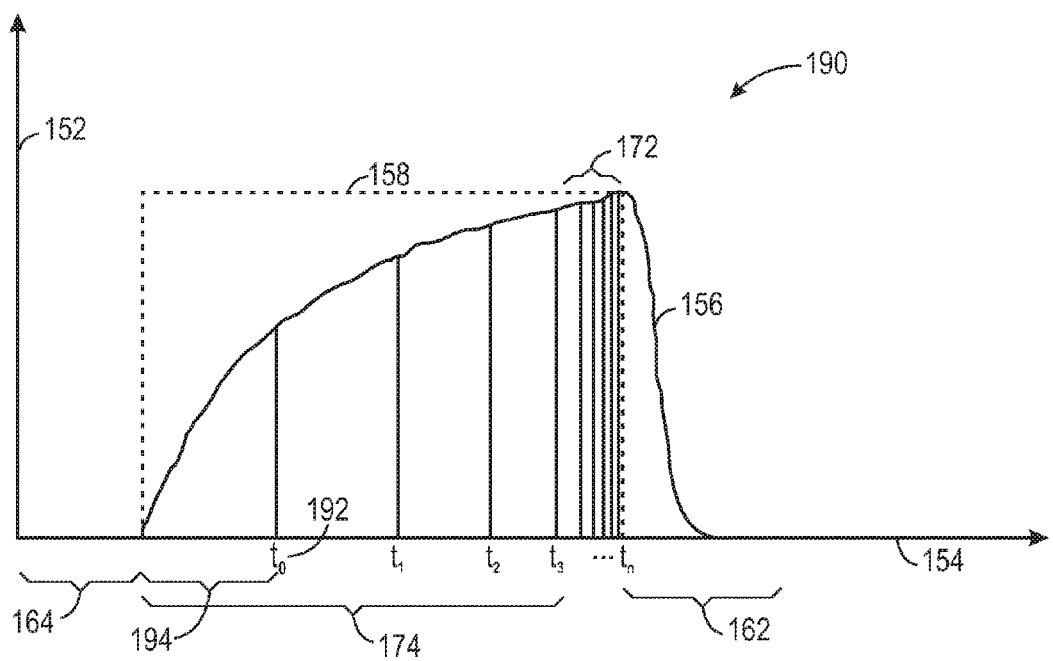
FIG. 6 is a graph depicting another method of exponential sampling of a light intensity signal, according to an embodiment.
Figure 7:
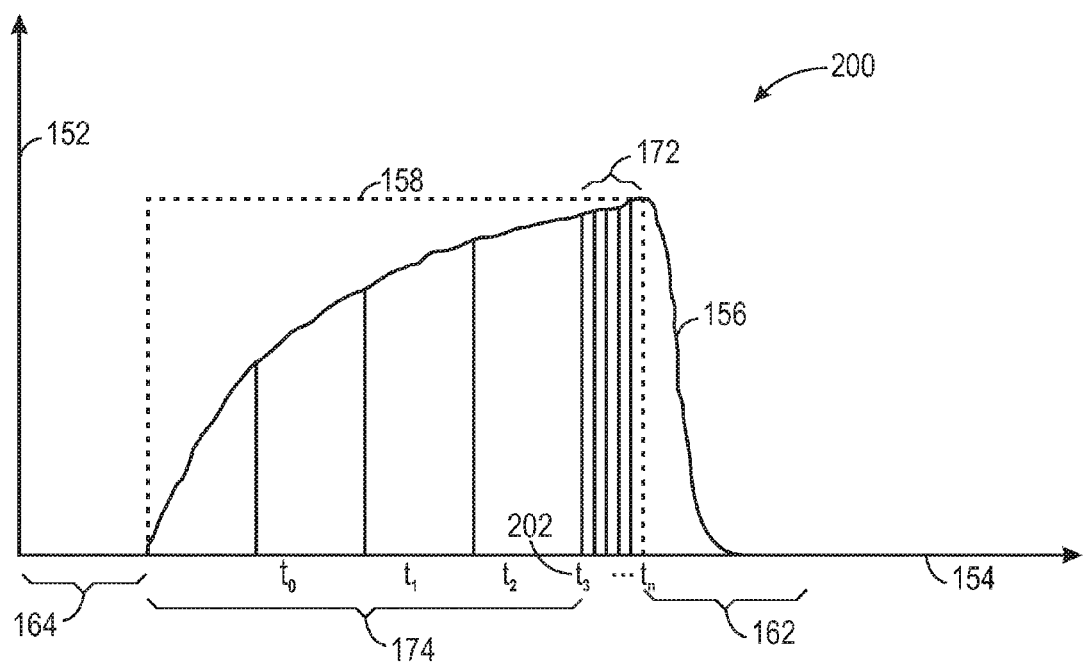
FIG. 7 is a graph depicting a Nyquist sampling method of a light intensity signal, according to an embodiment.

The graph 190 of FIG. 6 depicts another embodiment of sampling at a higher sampling density during a comparatively relevant portion 172 of a light intensity signal 156, in accordance with the present techniques. In one embodiment, the pulse oximeter 100 may begin sampling at the higher sampling density at a particular start time 192 in each pulse width period 158. The start time 192 may be based on known information about the signal 156 or known information about a typical waveform of a signal 156 in the pulse width period 158. For example, the pulse oximeter 100 may be programmed to start sampling at a start time 192 where the signal amplitude typically nears a maximum amplitude.

In one or more embodiments, the relevant period 172 may be sampled at a higher sampling density while an earlier portion 194 of the signal 156 in the pulse width period 158 before the start time 192 may not be sampled. For example, the earlier portion 194 may not be sampled, and once the signal 156 reaches the start time 192 of the pulse width period 158, the pulse oximeter 100 may begin to exponentially sample the relevant portion 172. In some embodiments, the earlier portion 194 may not be sampled, while the relevant portion 172 may be sampled at or above the Nyquist rate. In another embodiment, the relevant portion 172 may be sampled at a linearly increasing frequency. In yet another embodiment, the earlier portion 194 may not be sampled, while the relevant portion 172 is sampled at a frequency that is substantially proportional to the amplitude increase according to a typical waveform of the signal 156.

Alternatively, the earlier portion 194 may be sampled periodically, at a sampling density less than the sampling density during the relevant portion 172. In each of the above examples of increased sampling during the relevant portion 172, the earlier portion 194 may be either not sampled, or sampled periodically at a lower sampling density than that of the relevant portion 172. For example, in one embodiment, the earlier portion 194 may be sampled periodically at or below the Nyquist rate, and after the start time 192, the relevant portion 172 may be sampled at or above the Nyquist rate.

Sampling at an increased frequency starting from a start time 192 (e.g., sampling exponentially, sampling at or above the Nyquist rate, sampling at a linearly increasing frequency, sampling at a proportionally increasing frequency, etc. after the start time 192) may provide a more accurate digital signal. In embodiments, sampling at an increased frequency after the start time 192 may increase the probability of sampling the signal 156 at a maximum amplitude in each pulse width period 158. The pulse oximeter 100 may also save on processing power by reducing (or eliminating, in some embodiments) sampling during less relevant portions of the signal 156, such the earlier portion 194. Further, the dark periods 162 may still be sampled periodically (not shown) for purposes such as filtering and/or removing noise such as ambient light contribution to the light intensity signal 156.

In another embodiment, a sampling method of the present techniques may be based on the waveform and the Nyquist rate of the signal 156. As depicted in the graph 200 of FIG. 7, the signal 156 may be sampled at different frequencies throughout a pulse width period 158. For example, the pulse oximeter 100 may use a sampling frequency which may be lower than the Nyquist rate of the signal 156, until the start time 202, which may be based on a time during a pulse width period 158 when a signal 156 typically nears a maximum amplitude. The pulse oximeter 100 may then sample above the Nyquist rate (e.g., oversample) after the start time 202. Thus, the relevant portion 172 of the signal 156 during the pulse width period 158 may be oversampled to increase the probability of producing a more accurate digitized signal. In other embodiments, the portion of the signal 156 in the pulse width period 158 prior to a start time 202 (i.e., the earlier portion 174) may not be sampled at all to further save on processing power. In some embodiments, the dark periods 162 of the signal 156 may be sampled periodically, for example, at a frequency lower than the Nyquist rate. Using a lower sampling density during portions of the signal 156 where a high sampling frequency may be less beneficial may save on processing power of the pulse oximeter 100. Meanwhile, using a high sampling density during relevant portions 172 of the signal 156 may improve a digitized signal, and may improve the accuracy of the physiological characteristics calculated from the digitized signal.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, methemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A method of processing a signal from a pulse oximetry sensor, comprising:
   using a pulse oximeter, providing a time-multiplexed drive signal to the pulse oximetry sensor to drive a red emitter of the pulse oximetry sensor during a red pulse width period and to drive an infrared emitter of the pulse oximetry sensor during an infrared pulse width period;
   using the pulse oximeter, detecting a light intensity signal in response to the time-multiplexed drive signal; and
   using the pulse oximeter, increasing a sampling rate of the light intensity signal substantially in proportion to an expected amplitude of the light intensity signal during the red pulse width period and the infrared pulse width period, wherein the sampling rate is below a Nyquist rate during a first red portion of the red pulse width period and during a first infrared portion of the infrared pulse width period, and wherein the sampling rate is at or above the Nyquist rate during a second red portion of the red pulse width period subsequent to the first red portion and during a second infrared portion of the infrared pulse width period subsequent to the first infrared portion.

2. The method of claim 1, comprising using a processor to calculate an oxygen saturation value based at least in part on the sampled light intensity signal.

3. The method, as set forth in claim 1, wherein increasing the sampling rate comprises oversampling the light intensity signal toward an end of the red pulse width period and an end of the infrared pulse width period.

4. The method, as set forth in claim 1 wherein the second red portion-comprises a first maximum amplitude of the light intensity signal during the red pulse width period, and the second infrared portion comprises a second maximum amplitude of the light intensity signal during the infrared pulse width period.

5. The method of claim 1, wherein the Nyquist rate is approximately 1211 hertz.

6. The method of claim 5, wherein the sampling rate in the second red portion and the second infrared portion is approximately 4844 hertz.

* * * * *